US012629329B2

(12) United States Patent (10) Patent No.: US 12,629,329 B2

Hasjim et al. (45) Date of Patent: May 19, 2026

(54) NATIVE AND POROUS STARCH AS WHITE PIGMENT IN TOOTHPASTE

(71) Applicant: ROQUETTE FRERES, Lestrem (FR)

(72) Inventors: Jovin Hasjim, Shanghai (CN); Guangyu Zhang, Shanghai (CN); Jia Li, Shanghai (CN); Bernard Pora, Shanghai (CN)

(73) Assignee: Roquette Freres, Lestrem (FR)

( * ) Notice: Subject to any disclaimer, the term of this patent is extended or adjusted under 35 U.S.C. 154(b) by 728 days.

(21) Appl. No.: 17/758,552

(22) PCT Filed: Jan. 12, 2021

(86) PCT No.: PCT/EP2021/050454

§ 371 (c)(1),
(2) Date: Jul. 8, 2022

(87) PCT Pub. No.: WO2021/144245

PCT Pub. Date: Jul. 22, 2021

(65) Prior Publication Data

US 2023/0049362 A1     Feb. 16, 2023

(30) Foreign Application Priority Data

Jan. 14, 2020   (CN) .......................... 202010038301.9

(51) Int. Cl.
*A61K 8/73*       (2006.01)
*A61K 8/02*       (2006.01)
*A61Q 11/00*     (2006.01)

(52) U.S. Cl.
CPC ............ *A61K 8/732* (2013.01); *A61K 8/0279* (2013.01); *A61Q 11/00* (2013.01); *A61K 2800/30* (2013.01); *A61K 2800/43* (2013.01)

(58) Field of Classification Search
None
See application file for complete search history.

(56) References Cited

U.S. PATENT DOCUMENTS

| | | | |
|---|---|---|---|
| 4,508,713 A | | 4/1985 | Stroz et al. |
| 5,084,268 A | * | 1/1992 | Thaler .................. A61K 8/8147 |
| | | | 424/53 |
| 5,208,010 A | | 5/1993 | Thaler |
| 2002/0144629 A1 | | 10/2002 | Malkki et al. |

| | | | |
|---|---|---|---|
| 2004/0043134 A1 | * | 3/2004 | Corriveau ............... A23P 20/20 |
| | | | 426/658 |
| 2007/0163737 A1 | | 7/2007 | Teknillinen |
| 2013/0251645 A1 | * | 9/2013 | Won ......................... A61K 8/27 |
| | | | 264/165 |
| 2016/0243017 A1 | * | 8/2016 | Joshi ...................... A61K 8/732 |
| 2022/0401341 A1 | | 12/2022 | Hilmer et al. |

FOREIGN PATENT DOCUMENTS

| | | |
|---|---|---|
| FR | 1033530 A | 7/1953 |
| GB | 2162864 B | 3/1988 |
| JP | H1179963 A | 3/1999 |
| JP | 2000119149 A | 4/2000 |
| JP | 2002533374 A | 10/2002 |

OTHER PUBLICATIONS

Nieburg, Confectionary News, 2017, pp. 1-10. (Year: 2017).*
Chen et al., Int. J. Bio. Macromol., 2020, vol. 144, pp. 656-662 (Year: 2020).*
Anonymous, "Natural Complete Care Toothpaste", XP055797985, Database GNPD [Online] Mintel; Jan. 9, 2019 (Jan. 9, 2019), Database accession No. 6253387; abstract.
Anonymous, "Power White Deep Stain Eraser Fluoride Toothpaste", XP055797988, Database GNPD [Online] Mintel; Jul. 4, 2016 (Jul. 4, 2016), Database accession No. 4118663; the whole document.
Anonymous, "Coconut & Peppermint Blooming Whitening Mouthwash", XP055798117, Database GNPD [Online] Mintel; Oct. 1, 2019 (Oct. 1, 2019), Database accession No. 6918305; the whole document.
Anonymous, "Wild Strawberry and Cherry Natural Toothpaste for Kids", XP055798128, Database GNPD [Online] Mintel; Jun. 28, 2019 (Jun. 28, 2019), Database accession No. 6672787; the whole document.
The English translation of the Japanese Office Action, mailed on Dec. 3, 2024, in the related Japanese Patent Application No. 2022-542440.
The International Search Report and Written Opinion, mailed on May 4, 2021, in the corresponding PCT Appl. No. PCT/EP2021/050454.
The Communication pursuant to Article 94(3) EPC, mailed on Sep. 11, 2025 in the related European Patent Application No. 21701403.4.

* cited by examiner

*Primary Examiner* — Brian Gulledge

(57) ABSTRACT

The present invention relates to the use of native and/or porous starch as white pigment in dental health products and in particular in toothpastes. The present invention also relates to the process of fabricating a dental health product composition and in particular a toothpaste composition.

13 Claims, 2 Drawing Sheets

NATIVE AND POROUS STARCH AS WHITE PIGMENT IN TOOTHPASTE

FIELD OF THE INVENTION

The present invention relates to the use of native and/or porous starch as white pigment in dental health products and in particular in toothpastes. The present invention also relates to the process of fabricating a dental health product composition and in particular a toothpaste composition.

BACKGROUND

Toothpaste compositions generally contain an abrasive agent and a gelling agent in a liquid medium consisting of a humectant and various ingredients such as flavors, colorants, white pigments, preservatives, detergents, anti-tartar agents, antibacterial agents, and the like. Typical white pigments used in toothpastes are titanium dioxide. However, recent studies have recognized titanium dioxide particles as emerging pollutants (Hazardous Effects of Titanium Dioxide Nanoparticles in Ecosystem, Syed Niaz Ali Shah et al., Bioinorganic Chemistry and Applications. Volume 2017, Article ID 4101735, 12 pages) and as being harmful to human health (Titanium dioxide in our everyday life; is it safe?, Matej Skocaj et al., Radiol Oncol. 2011 December; 45(4): 227-247)(Titanium dioxide nanoparticles: a review of current toxicological data, Hongbo Shi, Particle and Fibre Toxicology volume 10, Article number: 15 (2013)).

There is thus a need to provide more environmentally friendly and less toxic white pigments for dental health products such as toothpastes.

The present inventors have surprisingly found that native and/or porous starch can be used as non-chemical, environmentally friendly white pigment in dental products and in particular in toothpastes. In particular, native and porous starches are toothfriendly, are perceived as a natural and healthy ingredient by the consumers, and do not have tolerance issues.

SUMMARY OF THE INVENTION

A first object of the present invention is directed to the use of starch as white pigment to replace titanium dioxide in a dental health product composition, the starch being a native starch, a porous starch or a mixture thereof.

A second object of the present invention relates to a dental health product composition and in particular a toothpaste composition comprising a white pigment containing or consisting of a native starch, a porous starch or a mixture thereof.

A third object of the present invention relates to a process of fabricating the dental health product composition of the present invention, in particular the toothpaste composition of the present invention, comprising the step of adding a native starch, a porous starch or a mixture thereof as white pigment.

A fourth object of the present invention relates to a dental health product composition, in particular a toothpaste composition obtained from the process of the present invention.

DETAILED DESCRIPTION

A first object of the present invention is directed to the use of starch as white pigment to replace titanium dioxide in a dental health product composition, the starch being a native starch, a porous starch or a mixture thereof.

As used herein the expression "dental health product" refers to toothpastes, chewing gums, and preferably toothpastes.

As used herein the expression "native starch" refers to starch coming from natural sources. It does not result from enzymatic or chemical processing methods. Typical native sources for the starches are cereal, tubers, roots, legumes and fruits. In the present invention, native starch may be recovered from native sources such as tapioca, waxy tapioca, maize, pea, potato, waxy potato, wheat, waxy wheat, waxy maize, high-amylose maize, mung bean, rice, waxy rice, sweet potato, waxy sweet potato, millet, sago, sorghum, *quinoa*, arrowroot, amaranth, lotus root and buckwheat by extraction processes. Native starch is normally extracted using either wet milling or dry milling known process.

An example of a first starch extraction process comprises the following steps:

1) cleaning of grain kernels from foreign matters;
2) steeping of the grain in water, alkaline solution or a solution containing a reducing agent to soften the kernels and to facilitate the separate of starch and protein;
3) optionally, coarse grinding followed by hydrocyclone to remove the germ from the kernel;
4) fine grinding of the remaining grain kernel to release the fiber, protein, and starch;
5) passing through screens with various opening sizes to separate fiber from protein and starch;
6) optionally, removing the excess water in slurry containing starch and protein;
7) separating protein from starch by density, such as using multiple-stage hydrocyclone;
8) drying the starch, such as using centrifugal filter, vacuum filter, belt-type dryer, and/or flash dryer;
9) recovering the dried starch.

Another example of a second starch extraction process comprises the following steps:

1) cleaning and washing of starchy root or tuber from dirt and sticks;
2) removing the peel of the starchy root or tuber and chopping the flesh into chunks;
3) pulverizing the roots into pulpy slurry;
4) removing the coarse and fine fiber from starch slurry by screens and/or filter cloths with large and fine opening sizes;
5) concentrating starch slurry using two- or three-phase separator or a series of hydrocylone;
6) dewatering the starch using centrifuge or high-pressure filtration or press filter;
7) drying the starch using flash dryer;
8) recovering the dried starch.

Advantageously, the extraction process is free of organic solvents and free of chemical reactants. There is no chemical transformation. Thus, the dental health products, and in particular toothpastes, incorporating the native starch obtained from the extraction process can be clean labeled dental health products, and in particular clean labeled toothpastes.

The native starch useful for the present invention is not gelatinized but is under granular form.

In a preferred embodiment of the present invention, the starch is a porous starch.

As used herein the expression "porous starch" refers to a granular starch that has been hydrolyzed by one or multiple amylolytic enzymes until multiple pores are visible on the surface of the starch granules by microscopic technique.

According to the present invention, porous starch may be produced through an enzymatic hydrolysis of native starch granules with one or multiple amylolytic enzymes, such as α-amylase and amyloglucosidase, at a temperature inferior to the gelatinization temperature of the starch. The native starch granules may be based on tapioca, waxy tapioca, maize, pea, potato, waxy potato, wheat, waxy wheat, waxy maize, high-amylose maize, mung bean, rice, waxy rice, sweet potato, waxy sweet potato, millet, sago, sorghum, *quinoa*, arrowroot, amaranth and buckwheat.

The particle size of the resulting porous starch granules may be further reduced by grinding, homogenization or micronization.

Acid, such as hydrochloric acid and sulfuric acid, can be used to hydrolyze the native starch or the porous starch to weaken the granular structure prior to enzyme hydrolysis or prior to physical modification (such as grinding, homogenization or micronization).

The resulting starch granules may have a porous structure on the surface and inside the granules. Preferably, they have a high number of large and small pores, which may or may not be connected to the hilum though internal channels.

In a preferred embodiment of the present invention, the porous starch used in the present invention has multiple pores on the surface with a diameter comprised between 0.01 μm and 5 μm, preferably between 0.05 μm and 2.5 μm, and more preferably between 0.1 μm and 1 μm.

The porosity can be observed using scanning electron microscopy.

In a preferred embodiment of the present invention, the porous starch used in the present invention has a particle diameter comprised between 0.5 μm and 200 μm, preferably between 1 μm and 100 μm, and more preferably between 2 μm and 60 μm.

The particle diameter may be measured by laser diffraction particle sizer (Beckman Coulter LS 13 320).

In the present invention, the starch may be selected from the group consisting of tapioca starch, waxy tapioca starch, maize starch, pea starch, potato starch, waxy potato starch, wheat starch, waxy wheat starch, waxy maize starch, high-amylose maize starch, mung bean starch, rice starch, waxy rice starch, sweet potato starch, waxy sweet potato starch, millet starch, sago starch, sorghum starch, *quinoa* starch, arrowroot starch, amaranth starch, lotus root starch and buckwheat starch.

In a preferred embodiment of the present invention, the porous starch used in the present invention is not gelatinized but is under granular form.

As used herein, the expression "white pigments" refers to a compound that changes the color of reflected or transmitted light as the result of wavelength-selective absorption.

Typical white pigments used in toothpaste are titanium dioxide.

In a preferred embodiment of the present invention, the starch replaces up to 30%, preferably up to 60% and more preferably up to 100% by weight of the titanium dioxide in the dental health product composition, in particular in the toothpaste composition.

In a preferred embodiment of the present invention, the native starch represents from 0.5% to 30%, preferably from 1% to 20% and more preferably from 2% to 15%, and even more preferably from 5 to 10% by weight with respect to the total weight of the dental health product composition, in particular of the toothpaste composition.

In a preferred embodiment of the present invention, the porous starch represents from 0.5% to 30%, preferably from 1% to 20% and more preferably from 2% to 15%, and even more preferably from 5 to 10% by weight with respect to the total weight of the dental health product composition, in particular of the toothpaste composition.

The dental health product composition of the present invention and in particular the toothpaste composition of the present invention may further comprise abrasives, humectants, surfactants, thickening agents and optionally additives.

Abrasive is the powder material that is the main part of the toothpaste formula, giving the function of tooth cleaning. Its function is to remove the dirt on the tooth surface, give luster, and, at the same time, do not wear the teeth.

Examples of suitable abrasives comprise but are not limited to, calcium carbonate, dicalcium phosphate, silica, aluminum hydroxide, calcium pyrophosphate, dicalcium phosphate dihydrate or a mixture thereof.

Typically, the abrasives represent from 10% to 25% (low abrasive toothpaste, like silica), or from 25% to 50%, and preferably from 30% to 50% (high abrasive toothpaste, like calcium carbonate/dicalcium phosphate) by weight with respect to the total weight of the dental health product composition and preferably of the toothpaste composition.

In a preferred embodiment of the present invention, water represents from 0% to 40%, preferably from 10% to 30% and even more preferably from 15% to 25% by weight with respect to the total weight of the dental health product composition and preferably of the toothpaste composition.

Humectant is used to keep the toothpaste within certain level of moisture, viscosity and smoothness, to prevent the paste from hardening and to render the paste easy to extrude from the tube; another function is to reduce the freezing point of the toothpaste so that it can be used in cold areas.

In a preferred embodiment of the present invention, the humectants are selected from glycerin, sorbitol, propylene glycol, butanediol, polyethylene glycol and mixtures thereof.

The humectants represent from 10% to 70%, preferably from 20% to 60%, and more preferably from 30% to 50% by weight with respect to the total weight of the dental health product composition, and preferably of the toothpaste composition.

Surfactants are used to provide a toothpaste with the ability of decontamination and of foaming.

Examples of surfactants comprise, but are not limited to, sodium lauryl sulfate, sodium lauroylmethylamine acetate, sodium lauryl alcohol sulfonate, sodium glyceryl monolaurate sulfonate, sodium dioctyl sulfonated succinate.

The surfactants represent from 0.01% to 10%, preferably 0.1% to 7%, and more preferably from 1 to 4%, by weight with respect to the total weight of the dental health product composition and preferably of the toothpaste composition.

Thickening agents aim to provide a toothpaste with texture, fluidity and stability.

In a preferred embodiment of the present invention, the thickening agents are selected from carboxymethyl cellulose, carrageenan, xanthan gum and mixtures thereof.

The thickening agents represent from 0.01% to 10%, preferably from 0.1% to 5%, and more preferably from 1% to 2% by weight with respect to the total weight of the dental health product composition and preferably of the toothpaste composition.

In a preferred embodiment of the present invention, the additives are selected from, flavoring agents, sweeteners, preservatives, colorants, anti-tartar agents, others and mixtures thereof.

The additives represents from 0% to 10%, preferably from 0.1% to 7% by weight, and more preferably from 1% to 4% by weight with respect to the total weight of the dental health product composition and preferably of the toothpaste composition.

All types of flavoring agents well known in the art may be added to the dental health product composition of the present invention and in particular of the toothpaste composition of the present invention. Flavoring agents may comprise essential oils, synthetic flavors, and mixtures thereof including but not limited to oils derived from plants and fruits such as citrus oils, fruit essences, peppermint oil, spearmint oil, clove oil, oil of wintergreen, anise, and the like. Artificial flavoring agents can also be contemplated. Those skilled in the art will recognize that natural and artificial flavoring agents may be combined in any sensorially acceptable blend.

Examples of sweeteners comprise, but are not limited to, sodium sacharin, neotame, sucralose, aspartame, *stevia* extract (or steviol glycosides), acesulfame K, sugar alcohols (such as sorbitol, xylitol, maltitol, and erythritol), luohanguo extract, and mixtures thereof.

Preservatives refer to substances that prevent dental health product from putrefying and deteriorating and extend the shelf life of dental health products. Examples of preservatives comprise, but are not limited to, methyl p-hydroxybenzoate, propyl p-hydroxybenzoate, ethyl p-hydroxybenzoate and mixtures thereof.

Examples of colorants comprise, but are not limited to lutein, lycopene, zeaxanthin, brilliant blue, and mixtures thereof.

Examples of anti-tartar agents comprise, but are not limited to sodium monofluorophosphate, and mixtures thereof.

Examples of others additives comprise, but are not limited to, ethanol.

In a preferred embodiment of the present invention, the dental health product composition and in particular the toothpaste composition comprises:

from 0.5% to 30%, preferably from 1% to 20% and more preferably from 2% to 15%, and even more preferably from 5 to 10% by weight of native starch with respect to the total weight of the dental health product composition, in particular of the toothpaste composition, from 0.5% to 30%, preferably from 1% to 20% and more preferably from 2% to 15%, and even more preferably from 5 to 10% by weight of porous starch with respect to the total weight of the dental health product composition, in particular of the toothpaste composition, optionally from 0% to 40%, preferably from 10% to 30%, and even more preferably from 15% to 25% by weight of water with respect to the total weight of the dental health product composition, in particular of the toothpaste composition, from 10% to 70%, preferably from 20% to 60%, and more preferably from 30% to 50% by weight of humectant with respect to the total weight of the dental health product composition, in particular of the toothpaste composition, optionally from 10% to 25% (low abrasive toothpaste, like silica), or from 25% to 50%, and preferably from 30% to 50% (high abrasive toothpaste, like calcium carbonate/dicalcium phosphate) by weight of abrasives with respect to the total weight of the dental health product composition, in particular of the toothpaste composition, from 0.01% to 10%, preferably 0.1% to 7%, and more preferably from 1 to 4% by weight of surfactants with respect to the total weight of the dental health product composition, in particular of the toothpaste composition, from 0.01% to 10%, preferably from 0.1% to 5%, and more preferably from 1% to 2% by weight of thickening agents with respect to the total weight of the dental health product composition, in particular of the toothpaste composition, and optionally from 0% to 10%, preferably from 0.1% to 7% by weight, and more preferably from 1% to 4% by weight of additives with respect to the total weight of the dental health product composition, in particular of the toothpaste composition.

The present invention also relates to a dental health product composition and in particular a toothpaste composition comprising a white pigment containing or consisting of a native starch, a porous starch or a mixture thereof as previously defined.

In a preferred embodiment of the present invention, the composition does not comprise titanium dioxide as white pigment.

Thanks to the specific dental health product composition, and in particular toothpaste composition, as previously defined it is possible to obtain a toothfriendly dental health product, and in particular toothpaste, having low fermentability, being noncariogenic and nonerosive, and without tolerance issues at all while having good mouthfeel and good processing properties. In particular, the dental health product and in particular the toothpaste is a toothfriendly dental health product, and in particular toothfriendly toothpaste, having a mouthfeel and flavor delivery characteristics similar and even improved to that of a dental health product, and in particular toothpaste, made with a titanium dioxide as white pigment. In particular, native starch and porous starch are non-chemical and environmentally friendly white pigments.

In the present invention "a toothfriendly dental health product" refers to a product that has low fermentability, noncariogenic and nonerosive potential in healthy people. In the same way, "a toothfriendly toothpaste" refers to a toothpaste that has low fermentability, noncariogenic and nonerosive potential in healthy people.

The "toothfriendly" properties of a dental health product, and in particular toothpaste, can be determined by intraoral pH-telemetry according to a standardized method (Toothfriendly International's Standard Operation Procedures) described in Imfeld, Th. N., *Identification of Law Caries Risk Dietary Components, Monographs in Oral Science*, Vol. 11, 198pp., H. M. Myers (*ed.*), S. Karger A G, Basel, 1983. In this standardized method, the pH of interdental plaque is measured during and for 30 minutes after the consumption or use of the dental health product and in particular of the toothpaste to be tested with a plaque-covered electrode. A dental health product, and in particular toothpaste, is considered to have low fermentability, noncariogenic and nonerosive potential if it does not depress the pH of the interdental plaque below 5.7 by bacterial fermentation, neither during consumption/use nor during a period of 30 minutes following consumption/use.

In particular, the present inventors have found that native and porous starch were not easily fermented by bacteria in the mouth thus the pH of the interdental plaque after the consumption or the use of dental health product in particular of the toothpaste does not drop to critical levels (pH 5.7). In a preferred embodiment of the present invention, the interdental plaque after the consumption or the use of the dental health product composition and in particular the toothpaste composition does not drop to a pH below 5.7, preferably the interdental plaque after the consumption or the use of the dental health product composition has a pH comprised between 5.7 and 7, and more preferably between 6 and 7.

The abrasion of the dental health product may tested according to the protocol described in Tawakoli et al., 2015, Swiss Dent J, 125, 1210-9.

Another aspect of the present invention is to make a toothfriendly dental health product composition and preferably toothpaste composition with native starch, porous starch or mixture thereof as white pigment, while keeping mouthfeel and flavor delivery characteristics similar and even improved to that of a dental health product composition, and in particular toothpaste composition, made with a titanium dioxide as white pigment. In particular, native starch and porous starch are non-chemical and environmentally friendly white pigments and do not have tolerance issues.

Thus, another object of the present invention relates to a process of fabricating the dental health product composition as previously defined, in particular the toothpaste composition as previously defined, comprising the step of adding native starch, porous starch or mixture thereof as white pigment.

In a preferred embodiment, the process of the present invention does not comprise a step of adding titanium dioxide as white pigment.

The dental health product composition of the present invention and in particular the toothpaste composition may be manufactured by sequentially adding the various dental health product ingredients to a commercially available mixer known in the art.

The present invention also relates to the dental health product composition, and in particular toothpaste composition, obtained from the process of the present invention.

The invention will now be illustrated by means of the following figures and examples, it being understood that these are intended to explain the invention, and in no way to limit its scope.

EXAMPLES

In the following examples, the following commercial products are used:

Neosorb 70/70B (liquid sorbitol) commercialized by Roquette
Sodium lauryl sulfate commercialized by Sinopharm
Carboxymethyl cellulose commercialized by Ashland
Ethanol commercialized by Sinopharm
Flavor commercialized by IFF
Sodium saccharin commercialized by Sinopharm
Methyl p-hydroxy benzoate commercialized by Sinopharm
Propyl p-hydroxybenzoate commercialized by Sinopharm
Sodium monofluorophosphate commercialized by Sinopharm The native waxy maize starch used in example 1 was produced according to the protocol mentioned in the first example of starch extraction process described in the description.

The porous waxy maize starch used in example 2 was produced from the native waxy maize according to the following protocol.

1. Suspending native waxy maize starch in decarbonated water to 26% solid content.
2. Adjusting pH of starch slurry to 7.0 using 3.3% NaOH solution.
3. Adding thermosable α-amylase (Liquozyme Supra from Novozymes, 2.67 mg enzyme/g dry starch) and reacting at 55° C. for 4 hours.
4. Stopping the reaction by adjusting the pH to 3-3.5 using 5% hydrochloric solution and holding for one hour.
5. Adjusting back the pH to 4.5-5.5 using 3.3% sodium hydroxide solution.
6. Cooling the starch slurry to about 25° C.
7. Press filtering the slurry to obtain porous starch cake.
8. Washing the cake with decarbonated water.
9. Drying the cake using a flash dryer into powder with moisture content below 12%.

Figure 1:
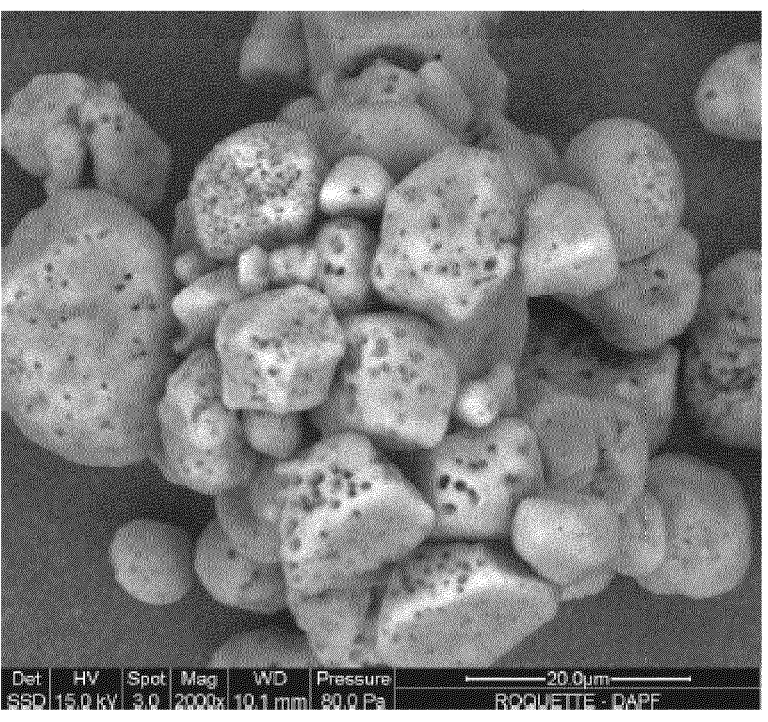
FIG. 1: scanning electron micrograph of porous waxy maize starch

The scanning electron micrograph of porous waxy maize starch is shown on FIG. 1.

Example 1: Analysis of Abrasivity and Fermentability of Toothpaste Made Using Native Waxy Maize Starch The recipe of the toothpaste sample to be tested is presented in table 1.

TABLE 1

| Ingredients | Percentage by weight (%) |
|---|---|
| Neosorb 70/70B (liquid sorbitol) (humectant) | 45.00 |
| Water | 20.00 |
| Waxy maize starch (white pigment/potential abrasive) | 28.4 |
| Sodium lauryl sulfate (surfactant) | 3.00 |
| Carboxymethyl cellulose (thickening agent) | 1.2 |
| Ethanol | 1.00 |
| Flavor (flavoring agent) | 1.00 |
| Sodium saccharin (sweetener) | 0.2 |
| methyl p-hydroxy benzoate (preservative) | 0.18 |
| propyl p-hydroxybenzoate (preservative) | 0.02 |
| Sodium monofluorophosphate (anti-tartar agent) | 0.76 |

The toothpaste sample was prepared according to the following protocol:

1. Preparing a first solution by dissolving sodium saccharin and sodium monofluorophosphate in water at 50° C.
2. Preparing a second solution by adding the preservatives to the NEOSORB 70/70B sorbitol solution at 80° C. This second solution is then cooled to 50° C. and the carboxymethyl cellulose is dispersed under conditions of vigorous agitation.
3. Adding the first solution to the second solution. Allowing the resulting mixture to stand for 30 minutes.
4. Vacuum-mixing for 5 minutes.
5. Adding half of the waxy maize starch and mixing for 10 minutes.

6. Adding the second half of the waxy maize starch and mixing for another 10 minutes.

7. Adding sodium lauryl sulfate solution and ethanol, followed by 3 minutes of mixing.

8. Finally, adding flavoring agent and mix for 5 minutes under vacuum.

The "toothfriendly quality" of the resulting toothpaste was tested by using the pH-telemetric standardized method (Toothfriendly International's Standard Operation Procedures described in Imfeld, Th. N., *Identification of Law Caries Risk Dietary Components, Monographs in Oral Science*, Vol. 11, 198 pp., H. M. Myers (ed.), S. Karger A G, Basel, 1983). The sample has been tested in a volunteer having a 5-day old plaque.

Figure 2:
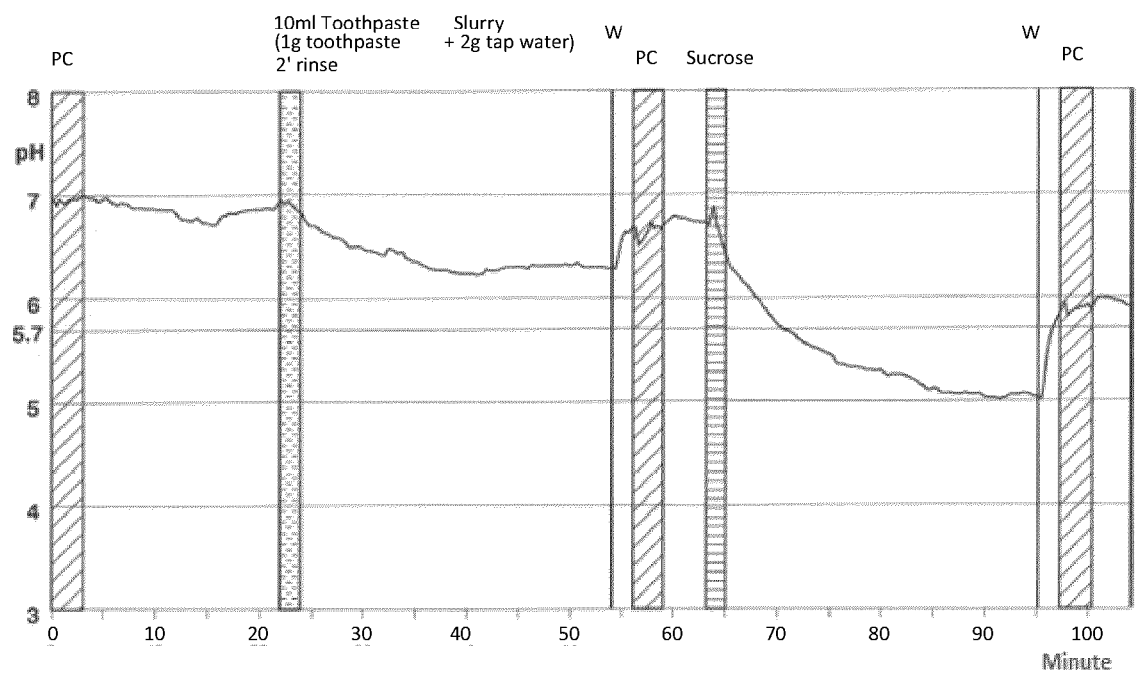
FIG. 2: pH-telemetry results of the toothpaste made with native waxy maize starch of example 1.

Results are shown on FIG. 2.

As shown on FIG. 2, the obtained plaque pH-curve demonstrated that the toothpaste sample was not associated with a depression of interdental plaque pH below 5.7, neither during nor after 30 min of swirling the toothpaste slurry in the mouth. The increase of the interdental plaque pH during water rising (W) and paraffin chewing (PC) as well as the drop of the interdental plaque pH below 5 following positive control treatment (with 10% sucrose solution) demonstrated the proper functioning of the plaque-covered electrodes. The obtained pH curve with the plaque-covered electrode demonstrated that the tested product also lacked of an erosive potential.

Thus, the toothpaste sample made using waxy maize starch has low fermentability (pH5.7).

The abrasion (RDA) of the toothpaste sample made using waxy maize starch was tested according to the following protocol.

Six bovine tooth roots were radioactively irradiated. Due to the irradiation, the phosphorus of the apatite was changed to radioactive $^{32}$P and gamma radiation. The roots were embedded in an acrylic resin and later brushed using an automatized 8 placebrushing machine for 25 min with a total of 1,500 horizontal brushing strokes (60 strokes per min). The brushing load was amounted to 2.5 N. As a reference toothbrush, manual toothbrushes with a plane bristle layout (Paro M43 medium, Esro AG) were used. The brushing medium was either a slurry prepared from the toothpaste sample or a slurry prepared from a standard abrasive. For the slurry preparation, 25 g toothpaste, 40 mL artificial saliva and 50 µL silicon anti anti-frothing agent (Fluka Chemie) were dispersed for 5 min. The standard slurry was prepared by mixing 10 g ISO Sident, 50 g solution from carboxymethyl cellulose (0.5%), glycerine (10%) and artificial saliva. The brushing runs were performed in a so-called "sandwich" technique. The first run was performed with the standard abrasive slurry, followed by a run with the toothpaste slurry and finally with the standard abrasive slurry. After each run, 0.5 g of the used slurries were pipetted and the $^{32}$P-irradiation in "decays per minute" (dpm) were measured with a Phosphorimagers® (Molecular Dynamics). The amount of $^{32}$P in the slurry after brushing is a measure for the dental hard tissue abrasion of the tested products. The values for the standard abrasive slurry runs of the "sandwich" technique were averaged and set as 100. The relative dentine abrasion of the toothpaste sample was expressed as a percentage of the standard abrasive value.

The tested toothpaste sample presented an average RDA value of 2.05, which means that the toothpaste made using waxy maize starch falls in the category "rarely abrasive" (RDA 0-20) toothpaste (Tawakoli et al., 2015, Swiss Dent J, 125, 1210-9).

These results demonstrated that toothpaste made using waxy maize starch has no abrasive effects on teeth, lacks of cariogenic and erosive potential and hence is "toothfriendly".

Example 2: Analysis of Abrasivity and Fermentability of Toothpaste Made Using Porous Waxy Maize Starch The recipe of the toothpaste sample to be tested is presented in table 2.

TABLE 2

| Ingredients | Percentage by weight (%) |
|---|---|
| Neosorb 70/70B (liquid sorbitol) (humectant) | 45.00 |
| Water | 20.00 |
| Porous waxy maize starch (white pigment/potential abrasive) | 28.4 |
| Sodium lauryl sulfate (surfactant) | 3.00 |
| carboxymethyl cellulose (thickening agent) | 1.2 |
| Ethanol | 1.00 |
| Flavor (flavoring agent) | 1.00 |
| Sodium saccharin (sweetener) | 0.2 |
| methyl p-hydroxy benzoate (preservative) | 0.18 |
| propyl p-hydroxybenzoate (preservative) | 0.02 |
| Sodium monofluorophosphate (anti tartar agent) | 0.76 |

The toothpaste sample was prepared according to the protocol of example 1 wherein waxy maize starch has been replaced by porous waxy maize starch.

The "toothfriendly quality" of the resulting toothpaste was tested by using a pH-telemetric standardized method as in example 1. The product was tested in a volunteer having a 6-day old plaque.

Figure 3:
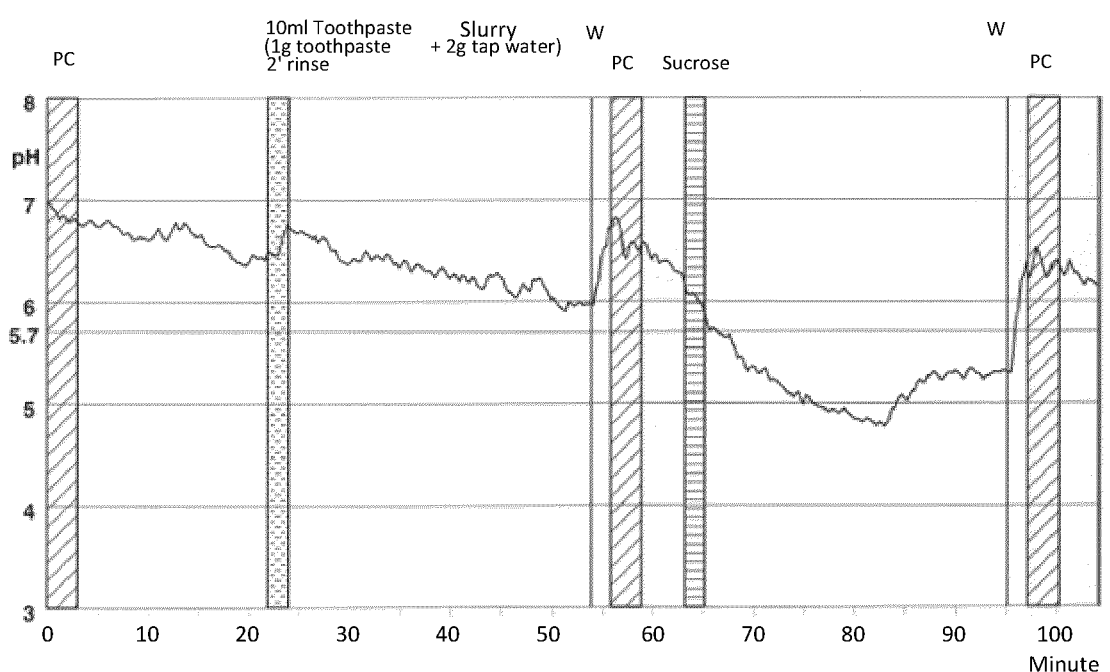
FIG. 3: pH-telemetry results of the toothpaste made with porous waxy maize starch of example 2.

Results are shown on FIG. 3.

As shown on FIG. 3, the obtained plaque pH-curve demonstrates that the toothpaste made with porous waxy maize starch was not associated with a depression of interdental plaque pH below 5.7, neither during nor after 30 min of swirling the toothpaste slurry in the mouth. The increase of the interdental plaque pH during water rising (W) and paraffin chewing (PC) as well as the drop of the plaque pH below 5 following positive control treatment (with 10% sucrose solution) demonstrated the proper functioning of the plaque-covered electrodes. The obtained pH curve with the plaque-covered electrode demonstrated that the tested product also lacked of an erosive potential.

Thus, the toothpaste made with porous waxy maize starch has low fermentability (pH≥5.7).

The abrasion (RDA) of the toothpaste sample made using porous waxy maize starch was tested according to the protocol of example 1.

The tested toothpaste made using porous waxy maize starch presented a RDA value of 1.3, which means that the toothpaste falls in the category "rarely abrasive" (RDA 0-20) toothpaste (Tawakoli et al., 2015, Swiss Dent J, 125, 1210-9).

These results demonstrated that toothpaste made using porous waxy maize starch has no abrasive effects on teeth, lacks of cariogenic and erosive potential and hence is "toothfriendly".

Conclusion: It was proven that when native and porous starches were used as white pigments in toothpastes, the resulting toothpastes had low abrasivity and low fermentability in the mouth.

The invention claimed is:

1. A method of formulating a dental health product composition having reduced or no titanium dioxide, the method comprising:

incorporating a starch selected from a native starch, a porous starch or a mixture thereof into the formulation of the composition, wherein the starch is incorporated to partially and/or totally replace the titanium dioxide required as white pigment in the formulation, wherein:

the native starch is an ungelatinized granular starch produced through a process involving no enzymatic or chemical processing steps, and wherein the native starch has a particle diameter comprised between 0.5 μm and 200 μm;

the porous starch is a granular starch produced through a process comprising a step of enzymatic hydrolysis of native starch granules with one or multiple amylolytic enzymes at a temperature inferior to the gelatinization temperature of the starch, and wherein the porous starch has a particle diameter comprised between 0.5 μm and 200 μm and has multiple pores on the surface with diameter comprised between 0.01 μm and 5 μm.

2. The method according to claim 1, wherein the starch is a porous starch.

3. The method according to claim 1, wherein the starch is selected from the group consisting of tapioca starch, waxy tapioca starch, maize starch, pea starch, potato starch, waxy potato starch, wheat starch, waxy wheat starch, waxy maize starch, high-amylose maize starch, mung bean starch, rice starch, waxy rice starch, sweet potato starch, waxy sweet potato starch, millet starch, sago starch, sorghum starch, quinoa starch, arrowroot starch, amaranth starch, lotus root starch and buckwheat starch.

4. The method according to claim 1, wherein the dental health product is selected from the group consisting of a toothpaste and a chewing gum.

5. The method according to claim 1, wherein the starch replaces up to 30%, by weight of the titanium dioxide required as white agent in the dental health product composition.

6. The method according to claim 1, wherein the starch is formulated in an amount in a range from 0.5% to 30% by weight with respect to the total weight of the dental health product composition.

7. The method according to claim 1, wherein the starch is formulated in an amount in a range from 1% to 30% by weight with respect to the total weight of the dental health product composition.

8. The method according to claim 1, wherein the dental health product is a toothpaste.

9. The method according to claim 1, wherein the starch replaces up to 60% by weight of the titanium dioxide required as white pigment in the dental health product composition.

10. The method according to claim 1, wherein the starch replaces up to 100% by weight of the titanium dioxide required as white pigment in the dental health product composition.

11. The method according to claim 1, wherein the starch is formulated in an amount in a range from 1% to 20% by weight with respect to the total weight of the dental health product composition.

12. The method according to claim 1, wherein the starch is formulated in amount in a range from 2% to 15% by weight with respect to the total weight of the dental health product composition.

13. The method according to claim 1, wherein the starch is formulated in an amount in a range from 5% to 10% by weight with respect to the total weight of the dental health product composition.

* * * * *